US012668556B2

(12) United States Patent 
Ouyang et al.

(10) Patent No.: US 12,668,556 B2 
(45) Date of Patent: Jun. 30, 2026

(54) CATALYSTS AND METHODS FOR METHANE DEHYDROGENATION

(71) Applicant: CHEVRON U.S.A. INC., San Ramon, CA (US)

(72) Inventors: Xiaoying Ouyang, San Ramon, CA (US); Alexander E. Kuperman, San Ramon, CA (US); Huping Luo, San Ramon, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 487 days.

(21) Appl. No.: 18/221,806

(22) Filed: Jul. 13, 2023

(65) Prior Publication Data

US 2024/0166578 A1 May 23, 2024

Related U.S. Application Data

(60) Provisional application No. 63/427,319, filed on Nov. 22, 2022.

(51) Int. Cl.
*C07C 2/76* (2006.01)
*B01J 21/08* (2006.01)
(Continued)

(52) U.S. Cl.
CPC .................. *C07C 2/76* (2013.01); *B01J 21/08* (2013.01); *B01J 35/23* (2024.01); *B01J 35/40* (2024.01);
(Continued)

(58) Field of Classification Search
CPC ......... C07C 2/76; C07C 2/84; C07C 2521/08; B01J 21/08; B01J 35/23; B01J 35/40; B01J 35/30; C01B 3/26; C01B 2203/1241
See application file for complete search history.

(56) References Cited

U.S. PATENT DOCUMENTS

| | | | |
|---|---|---|---|
| 4,617,060 A | 10/1986 | Dreibelbis | |
| 2003/0144565 A1* | 7/2003 | Allison ..................... | C07C 2/76 585/422 |

(Continued)

FOREIGN PATENT DOCUMENTS

| | | |
|---|---|---|
| WO | 1996000702 A1 | 1/1996 |
| WO | 2017040383 A1 | 3/2017 |

OTHER PUBLICATIONS

Šot et al. ("Non-oxidative Methane Coupling over Silica versus Silica-Supported Iron(II) Single Sites", Chem. Eur. J. 2020, 26, 8012-8016). (Year: 2020).*

(Continued)

*Primary Examiner* — Ali Z Fadhel

(74) *Attorney, Agent, or Firm* — HUNTON ANDREWS KURTH LLP

(57) ABSTRACT

The present application pertains to a methane dehydrogenation process subjecting a methane feed to a novel $SiO_2$ catalyst under dehydrogenation conditions and producing hydrogen, ethylene, an aromatic, or any mixture thereof. In another embodiment, the present application pertains to a novel catalyst for methane dehydrogenation. The catalyst comprises amorphous particles of $SiO_2$. The amorphous particles have a particle size with a nominal diameter of from about 5 nm to 1 cm. The amorphous particles of $SiO_2$ comprise a Lewis acidity sufficient to activate one or more C—H bonds in methane and generate one or more methyl radicals when the catalyst is subjected to methane dehydrogenation conditions. In another embodiment, the present application pertains to method of making the novel catalyst for methane dehydrogenation.

23 Claims, 6 Drawing Sheets

105 Heat calcine silica gel at 900 °C for one hour

(51) Int. Cl.
  B01J 35/23        (2024.01)
  B01J 35/40        (2024.01)
  C01B 3/26         (2006.01)
  C07C 2/84         (2006.01)

(52) U.S. Cl.
  CPC ................. C01B 3/26 (2013.01); C07C 2/84
        (2013.01); *C01B 2203/1241* (2013.01); *C07C
                                        2521/08* (2013.01)

(56)                References Cited

U.S. PATENT DOCUMENTS

2015/0140216 A1*  5/2015  Nelson ................. C23C 16/401
                                                      427/255.393
2021/0379549 A1   12/2021  Liu et al.

OTHER PUBLICATIONS

Supporting Information for Šot et al. ("Non-oxidative Methane Coupling over Silica versus Silica-Supported Iron(II) Single Sites", Chem. Eur. J. 2020, 26, 8012-8016). (Year: 2020).*
Notification Concerning Transmittal of International Preliminary Report on Patentability from related PCT Application No. PCT/US2023/080505, mailed Jun. 5, 2025, 10 pages.
International Search Report and Written Opinion dated Apr. 12, 2024 received in PCT/US2023/80505.

* cited by examiner

105 Heat calcine silica gel at 900 °C
for one hour

FIG. 1

505 A mixture of 1 mmol of iron(III) acetate and 10 g of quartz wool with a 4 μm nominal diameter are subjected to ball milling under N2 at 400 RPM for 12 hours 510 Next, the mixture is fused at 1650 °C for 5 hours in nitrogen 515 The calcined material is ball milled and sieved to produce the catalyst in the size of 20 – 40 mesh

CATALYSTS AND METHODS FOR METHANE DEHYDROGENATION

CROSS-REFERENCE TO RELATED APPLICATIONS

This application claims priority to U.S. Provisional Application No. 63/427,319 filed Nov. 22, 2022, the contents of which are incorporated herein in its entirety.

FIELD OF THE DISCLOSURE

The present application relates to fused silica catalysts and methods for methane dehydrogenation using the catalysts.

BACKGROUND

Natural gas is an efficient, abundant, and versatile energy source, of which the primary component is methane (CH4). Natural gas is one of the cleanest burning conventional fuels, producing lower levels of CO2 emissions than, for example, the heavier hydrocarbon fuels, such as coal and oil. Natural gas is also a primary source of raw material for hydrogen production. Traditionally, hydrogen has been produced via steam methane reforming (SMR) process. Unfortunately, even when achieving the maximum attenable $H_2$ yield from methane, SMR also produces a significant amount of $CO_2$ as a byproduct ($H_2:CO_2=4:1$). To reduce CO2 emissions often CCS (carbon capture sequestration) is integrated with SMR which adds complexity and cost to the process.

To date, utilization of methane for hydrogen production only takes up a small fraction of its overall consumption. Natural gas is still mainly used for its calorific value during its combustion into both $CO_2$ and $H_2O$, while its chemical value is underdeveloped. Today, raw chemicals (olefins, aromatics, etc.) are primarily produced from crude oil, of which the processes are complicated, costly, and polluting. A small fraction of raw chemicals, such as olefins, are currently converted from methane via intermediate syngas route, but such an indirect conversion is also complicated and carbon-intensive and costly.

Direct conversion of methane via oxidation reactions have been tried. Examples are oxidative coupling of methane to ethylene (OCM) and partial oxidation of methane to methanol and formaldehyde (SOM). Unfortunately, overoxidation often leads to low selectivity.

Methane dehydrogenation, also known as methane decomposition or methane pyrolysis or methane cracking has been tried to: (1) produce a "low-carbon" hydrogen and (2) produce raw chemicals from methane without going through a syngas. Unfortunately, such efforts like those using bifunctional catalysts based on Mo/zeolites have largely been failures due to, for example, the inability to achieve high selectivity to chemicals instead of coke and/or other inefficiencies.

It would be desirable if new methods and catalysts for converting methane into raw chemicals was developed. It would further be desirable if such new methods and catalysts could directly convert methane into useful products. It would further be desirable if such new methods and catalysts could provide high selectivity to one or more desired chemicals.

SUMMARY OF THE DISCLOSURE

In some aspects, the techniques described herein relate to a catalyst for methane dehydrogenation wherein the catalyst includes: amorphous particles of $SiO_2$; wherein the amorphous particles have a particle size with a nominal diameter of from about 5 nm to about 1 cm; and wherein the amorphous particles of $SiO_2$ include a Lewis acidity sufficient to activate C—H bonds in methane and generate methyl radicals when the catalyst is subjected to methane dehydrogenation conditions.

In some aspects, the techniques described herein relate to a methane dehydrogenation process including: subjecting a methane feed to a catalyst under dehydrogenation conditions, wherein the catalyst includes amorphous particles of $SiO_2$, wherein the amorphous particles have a particle size with a nominal diameter of from about 5 nm to about 1 cm, wherein the amorphous particles of $SiO_2$ include a Lewis acidity sufficient to activate C—H bonds in methane and generate methyl radicals when the catalyst is subjected to methane dehydrogenation conditions; and producing hydrogen, alkanes, alkenes, an aromatic, or any mixture thereof.

Further features of the disclosed systems and methods, and the advantages offered thereby, are explained in greater detail hereinafter with reference to specific example embodiments illustrated in the accompanying drawings.

BRIEF DESCRIPTION OF THE DRAWINGS

In order to facilitate a fuller understanding of the present invention, reference is now made to the attached drawings. The drawings should not be construed as limiting the present invention, but are intended only to illustrate different aspects and embodiments of the invention.

FIG. 1 illustrates a representative process for creating catalyst.

DETAILED DESCRIPTION

Figure 2:
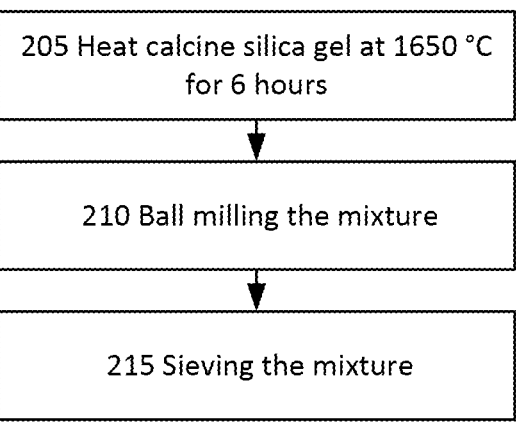
FIG. 2 illustrates a representative process for creating catalyst.

Exemplary embodiments of the invention will now be described in order to illustrate various features of the invention. The embodiments described herein are not intended to be limiting as to the scope of the invention, but rather are intended to provide examples of the components, use, and operation of the invention.

Furthermore, the described features, advantages, and characteristics of the embodiments may be combined in any suitable manner. One skilled in the relevant art will recognize that the embodiments may be practiced without one or more of the specific features or advantages of an embodiment. In other instances, additional features and advantages may be recognized in certain embodiments that may not be present in all embodiments.

The flowchart and block diagrams in the Figures illustrate the architecture, functionality, and operation of possible implementations of systems, methods, and products according to various embodiments of the present invention. In some alternative implementations, the functions noted in the block may occur out of the order noted in the figures. For example, two blocks shown in succession may, in fact, be executed substantially concurrently, or the blocks may sometimes be executed in the reverse order, depending upon the methods and products involved.

Advantageously, the present systems and methods solve one or more up to all of the aforementioned issues and more. For example, the process can convert natural gas to high value hydrocarbons and produce hydrogen as a carbon free fuel without significant carbon dioxide emissions. Regarding the catalyst, one embodiment describes a novel catalyst for methane dehydrogenation, comprising modified amorphous $SiO_2$ particles with, for example, an added Fe component. The catalyst's particle size may range from nanometers to centimeters, and the Fe additive, which can take various forms, may be present in various weight percentages. The Fe additive activates the C—H bonds in methane and generates methyl radicals during methane dehydrogenation. The amorphous particles may have a particle size with a nominal diameter of from about 5 nanometers to about 1 centimeter, preferably from about 50 nanometers to about 1 millimeter. The amorphous particles of $SiO_2$ may comprise silanol groups (—SiOH) with a Lewis acidity sufficient to activate C—H bonds in methane and generate methyl radicals when the catalyst is subjected to methane dehydrogenation conditions. The Fe additive may be in the forms of, but not limited to, Fe, $Fe_2O_3$, FeO, $Fe_3O_4$, $Fe(NO_3)_3$, $FeSO_4$, $FeCl_3$ and FeS. The weight percentage of such Fe additive may vary but is usually is from about 0.01% to about 25%, preferably from about 0.025% to about 5%.

New Catalysts and Processes for Making the Catalysts

This present invention is related to a novel catalyst and a method of methane dehydrogenation using the novel catalyst. The novel catalyst is generally a non-metallic derivative of fused silica (aka. fused quartz or quartz glass) as the catalyst. The products include hydrogen, olefins, alkanes, alkenes, aromatics, and coke, among which hydrogen, ethylene, benzene, and naphthalene may be the major products depending upon the selected conditions. Advantageously, these nonmetal oxide catalysts do not require the active component to be a metal.

Fused silica is a glass consisting of pure silica (silicon dioxide, $SiO_2$) in an amorphous form. It may be produced in any convenient manner. For example, it may be made by fusing (melting) high-purity silica sand, which consists of quartz crystals, or by burning $SiCl_4$ in a flame. Fused silica often has a very low surface area ($<1$ $m_2$/g BET surface area) and relatively little to no porosity since it is usually exposed to the fusion temperature ($\approx 1650°$ C.) during manufacturing. As described below, fused silica may be made into many useful forms, for example, reactor tubes, quartz frits, and/or quartz wool due to its high working temperature and chemical inertness under many conditions.

It has been discovered that the new catalyst's activity for methane dehydrogenation is often inversely correlated to the particle size of the fused silica under many reaction conditions. That is, the activity may typically increase after the fused silica is subjected to a size reduction process by means of, but not limited to, grinding, milling, cutting, hot melt extrusion, or any combination thereof.

The catalyst typically comprises amorphous particles of $SiO_2$. The size of the amorphous particles may vary depending upon the catalyst's desired use, desired products, and reaction conditions. Typically, the amorphous particles have a particle size with a nominal diameter of from about 5 nm to about 1 cm, preferably from about 50 nm to about 1 mm.

The catalyst may be made by any convenient process provided that the particles obtained comprise silanol groups with a Lewis acidity sufficient to activate C—H bonds in methane and generate methyl radicals when the catalyst is subjected to methane dehydrogenation conditions.

In some embodiments the process comprises reducing the size of a fused silica. The size reduction may be accomplished in any convenient manner although it is desirable in some embodiments that the size reduction increases a silanol to siloxane ratio in the catalyst. Useful size reduction techniques may include, for example, grinding, milling, cutting, hot melt extruding, or any combination thereof. After size reduction, if desired the reduced fused silica may be sieved to select a desired particle size. Sieve sizes may vary depending upon the catalyst's desired use, reaction conditions, desired products, and other factors. In some embodiments a sieved size may be from about 20 to about 40 mesh.

In the fused silica catalysts described herein a metal is not necessary and it may be preferred that the fused silica catalyst be non-metallic or at least substantially metal free. For example, the catalyst may comprise less than about 15, or less than about 10, or less than about 8 ppm of metals such as iron as analyzed by inductively coupled plasma spectroscopy. Thus, it is preferable that the catalyst herein comprises active sites that are not metallic. In some embodiments, the amorphous particles of $SiO_2$ in the catalyst comprise a plurality of non-hydrogen bonded silanol groups. The plurality of non-hydrogen bonded silanol groups may facilitate the catalyst in having a sufficient Lewis basicity as described above. The amount of non-hydrogen bonded silanol may vary from catalyst to catalyst. In some embodiments at least a portion of the silanol comprises non-hydrogen bonded silanol. In other embodiments a majority of the silanol may comprise non-hydrogen bonded silanol.

While not wishing to be bound by any particular theory, the surprising and unexpected catalyst activity observed may be due to a relatively low ≡Si—OH/≡Si—O—Si (silanol-to-siloxane) ratio in large fused silica particles due to their low geometric surface area. When the particle size is reduced mechanically, the ≡Si—OH/≡Si—O—Si≡ ratio increases, as some ≡Si—O—Si≡ are forced to open and convert to Si—OH. A portion, a majority, or even nearly all of the newly formed ≡Si—OH after the size reduction may be characterized as non-hydrogen-bonded ("nearly free surface") silanol groups by Raman and/or IR spectroscopies.

While not wishing to be bound by any particular theory, such non-hydrogen-bonded silanol groups might have sufficient Lewis acidity that can activate C—H bonds in methane molecules to generate methyl radicals, which produce hydrogen, hydrocarbons and carbon on the surface and in the gas phase through radical chain propagation and termination.

The fused silica catalyst is different from conventional Mo/zeolite catalysts. Methane decomposition over the Mo/zeolite catalyst follows a bifunctional pathway in which methane is activated and coupled to ethylene over Mo-carbide species, followed by ethylene aromatization over the zeolite Bronsted acid sites. In contrast, the fused silica catalyst follows a radical reaction pathway, in which C—H bond is activated in the presence of fused silica to produce methyl radicals, followed by chain propagation and termination. These two catalysts also generally operate at different temperatures. The Mo/zeolite catalyst may be run at temperatures below about 700° C., while the fused silica typically requires higher temperatures of up to 1100° C. or more.

Methods and Processes for Non-Oxidative Conversion of a Hydrocarbon to Hydrogen Using Novel Catalysts

The catalysts described above may be used in, for example, processes for non-oxidative conversion of a hydrocarbon such as natural gas to produce hydrogen and potentially other products. The process generally comprises contacting the hydrocarbon, e.g., natural gas, with a catalyst described above and/or a mixture of catalysts including one of the catalysts described above. The contacting is usually conducted under conditions to convert the hydrocarbon to hydrogen. The process may also produce a light hydrocarbon product such as ethylene, benzene, naphthalene, or any mixture thereof.

The methane dehydrogenation process typically comprises subjecting a methane feed to a catalyst under dehydrogenation conditions. The catalyst comprises amorphous particles of $SiO_2$. The amorphous particles have a particle size with a nominal diameter of from about 5 nm to about 1 cm, preferably from about 50 nm to about 1 mm. The amorphous particles of $SiO_2$ comprise a Lewis acidity sufficient to activate C—H bonds in methane and generate methyl radicals when the catalyst is subjected to methane dehydrogenation conditions.

Typically, hydrogen, ethylene, an aromatic, or any mixture thereof is produced. The aromatics may comprise an aromatic compound such as, for example, benzene, naphthalene, or any mixture thereof. If desired, the hydrogen and/or other products may be separated in any convenient manner.

The dehydrogenation conditions may vary widely depending upon the equipment, the methane feed composition, the specific catalyst composition, and other factors. Useful conditions in some embodiments may comprise a temperature of at least about 800° C. up to about 1200° C. and/or a residence time of from about 0.05 to about 100, or from about 0.05 to about 10 seconds, or from about 1 to about 7 seconds.

The content of methane in the methane feed may vary but in some embodiments it may comprise at least about 70%, or at least about 90% methane. The methane feed may comprise other components in amounts that do not significantly interfere with the process or desired products. In some cases, the methane feed may further comprise nitrogen.

Methane conversion and products produced may also vary depending upon the conditions, equipment, feed, specific catalyst composition, and other factors. In some embodiments, the methane conversion may be at least about 15%. In some embodiments, the process produces a mixture comprising hydrogen, ethylene, and an aromatic or a mixture of aromatics.

Various methods and processes are contemplated for making the new catalyst.

Figure 1:
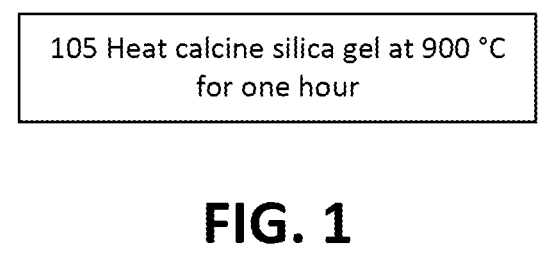

FIG. 1 illustrates a process for creating the catalyst as described with further reference above. The catalyst created by the process in FIG. 1 is referred to as Catalyst A. To prepare Catalyst A, silica gel (a type of material made from silicon dioxide) of a specific grade is heated in the presence of air at a temperature of 900° C. for 1 hour in action 105. This process is called calcination and it helps transform the silica gel into the desired catalyst form.

FIG. 2 illustrates a process for creating the catalyst as described with further reference above. The catalyst created by the process in FIG. 2 is referred to as Catalyst B. In action 205, silica gel of a technical grade is placed under a nitrogen atmosphere at a high temperature of 1650° C. for six hours. This process is called calcination and it helps transform the silica gel into the desired catalyst form. After calcination, in action 210 the material is subjected to ball milling (a grinding process using balls) and sieving to obtain particles within the size range of 20-40 mesh. The ball milling can be used to achieve a more uniform particle size distribution and to reduce the particle size of the material. In some embodiments, the calcined material is placed in a container along with the grinding balls, and the container is rotated to initiate the milling process. As a result of the ball milling, the calcined material is further fragmented into smaller particles. Following the ball milling step, in action 215 the material is sieved to separate particles based on their size. In this case, the sieving is performed to obtain particles within the desired size range of from about 20 to about 40 mesh. Sieving helps to select and separate particles that fall within the specified size range, ensuring that the final catalyst material meets the desired particle size requirements.

Figure 3:
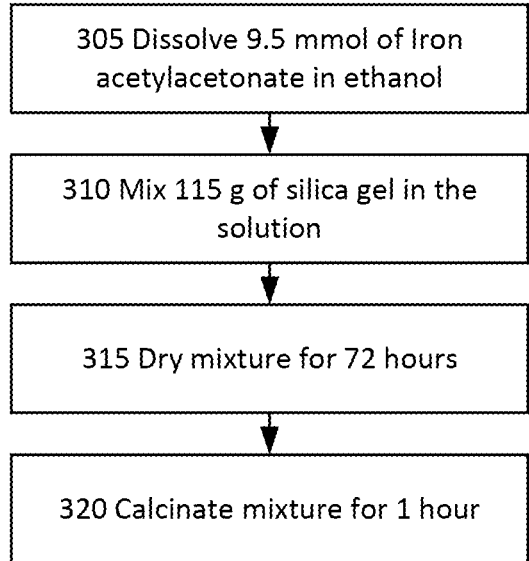
FIG. 3 illustrates a representative process for creating catalyst.

FIG. 3 illustrates a process for creating the catalyst as described with further reference above. The catalyst created by the process in FIG. 3 is referred to as Catalyst C. In action, 305, Catalyst C is prepared by dissolving iron(III) acetylacetonate (a chemical compound containing iron) in ethanol and mixing it with silica gel. The purpose of this step is to prepare a liquid solution of the iron compound, which will later be mixed with silica gel to incorporate iron into the catalyst. In action 310, 115 grams of silica gel can be mixed in with the liquid solution. In action 315, the mixture is then dried for 72 at least in some embodiments. The mixture of iron(III) acetylacetonate solution and silica gel is dried, typically by exposing it to air at a controlled temperature. Drying removes the solvent (ethanol) from the mixture, leaving behind solid materials. This step is employed to remove remaining liquid to ensure the stability of the catalyst. In action 320, the dried mixture is subjected to calcination, which involves heating the material at a high temperature of 900° C. for about 1 hour. This thermal treatment process induces chemical and structural changes in the materials to form the final catalyst structure and activate desired catalytic properties. The high temperature promotes reactions and transformations, resulting in the desired characteristics of Catalyst C. The presence of iron in the catalyst (Catalyst C) influences performance. Iron, being a transition metal, can act as a catalyst itself or modify the catalytic properties of the silica gel matrix. The addition of iron enhances certain reactions and/or improve the selectivity and efficiency of the catalyst in the processes.

Figure 4:
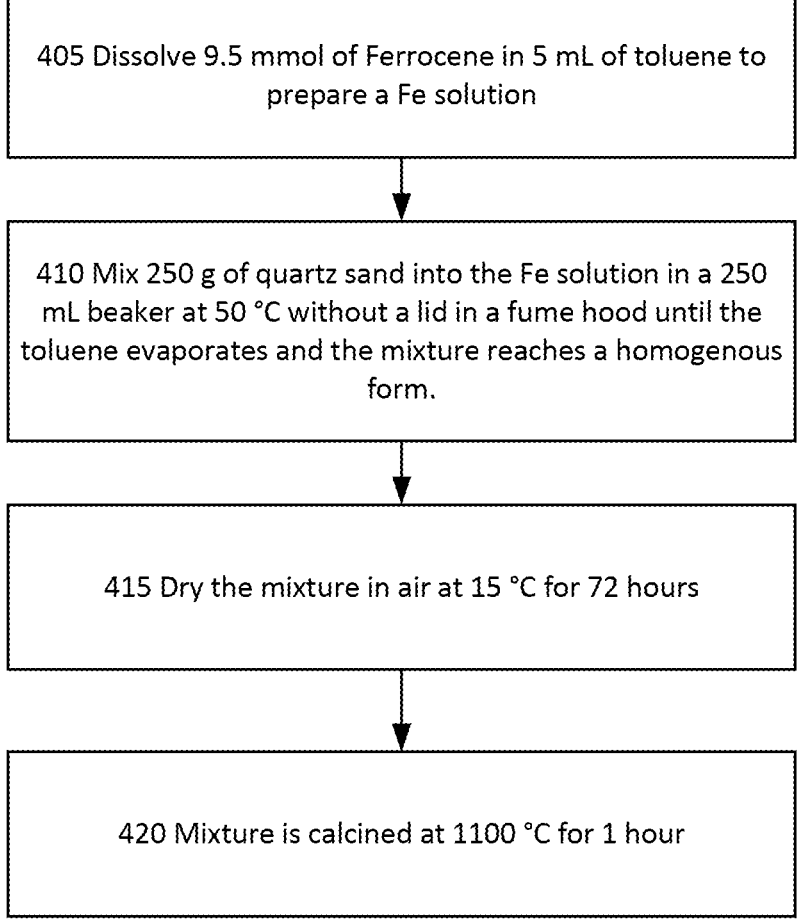
FIG. 4 illustrates a representative process for creating catalyst.

FIG. 4 illustrates a process for creating the catalyst as described with further reference above. The catalyst created by the process in FIG. 4 is referred to as Catalyst D. In 405, 9.5 mmol of ferrocene (containing iron) is dissolved in 5 mL toluene. Ferrocene is a chemical compound comprising iron, and it is dissolved in toluene to create a solution. Dissolving ferrocene in toluene prepares a liquid solution of the iron compound, which will later be mixed with quartz sand to incorporate iron into the catalyst. In action 410, the solution of ferrocene in toluene is combined with quartz sand, a type of crystalline silica material. The mixing process ensures that the iron compound is substantially uniformly distributed within the quartz sand matrix. By incorporating iron into the quartz sand, the catalyst's properties and behavior can be altered or enhanced. In one embodiment, 250 grams of quart sand are mixed into the Fe solution in a 250 mL beaker at 50° C. without a lid in a fumed hood until the toluene evaporates and the mixture reaches a homogenous form. In action 415, the mixture of ferrocene solution and quartz sand is dried, typically by exposing it to air at a controlled temperature. For example, the mixture can be dried in air at 15° C. for 72 hours. Drying removes the solvent (toluene) from the mixture, leaving behind solid materials. This removes residual liquid and ensures the stability of the catalyst. In action 420, the mixture is calcined at a high temperature of 1100° C. for 1 hour. The dried mixture is subjected to calcination. In this case, the mixture is heated to a temperature of 1100° C. for a duration of 1 hour. Calcination induces chemical reactions and structural changes in the materials, leading to the formation of the final catalyst structure and the activation of desired catalytic properties. The high temperature promotes reactions and transformations, ensuring the catalyst has the desired characteristics. The presence of iron in Catalyst D confers specific properties to the catalyst. Iron, being a transition metal, can act as a catalyst itself and/or modify the catalytic properties of the quartz sand matrix. The addition of iron is enhances certain reactions and/or improves the selectivity and efficiency of the catalyst in specific chemical processes. The exact impact of iron on the catalyst's properties and behavior often depends upon the specific reactions and conditions to which the catalyst is exposed.

Figure 5:
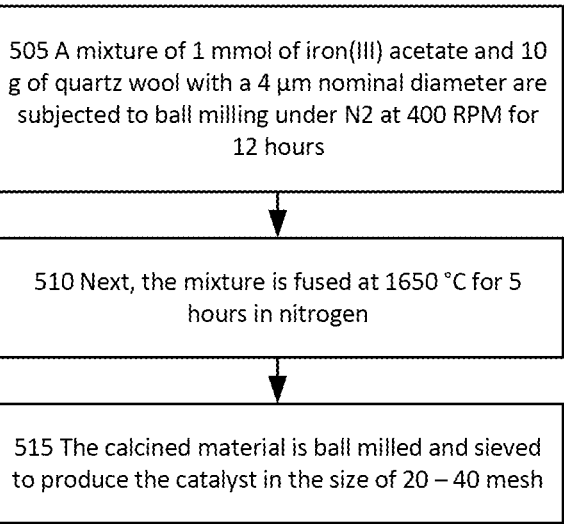
FIG. 5 illustrates a representative process for creating catalyst.

FIG. 5 illustrates a process for creating the catalyst as described with further reference above. The catalyst created by the process in FIG. 5 is referred to as Catalyst E. In action 505, a mixture of 1 mmol of iron(III) acetate and 10 grams of quartz wool (a type of fibrous quartz material) with a 4 μm nominal diameter is subjected to ball milling at N2 at 400 rpm for 12 hours. A comprising the iron compound and quartz wool matrix is formed. The specific composition and ratio of iron(III) acetate to quartz wool determines the concentration of iron in the catalyst and its distribution within the quartz wool structure. Ball milling promotes mixing, dispersion, and particle size reduction. It may also assist in achieving a more uniform distribution of iron within the quartz wool matrix, leading to improved catalytic properties. In action 510, the mixture is fused at a temperature of 1650° C. for 5 hours in nitrogen to achieve a substantially homogeneous and solidified structure. The high temperature causes the materials to fuse together, resulting in chemical interactions and transformations. In action 515, the resulting material is again subjected to ball milling and sieving to obtain the desired particle size of from about 20 to about 40 mesh. The resulting material from the fusion, ball milling, and sieving steps is identified as Catalyst E. The specific properties and catalytic behavior of Catalyst E may be influenced by the combination of iron(III) acetate with the quartz wool matrix, the structural changes induced by fusion at high temperature, and the refined particle size distribution obtained through ball milling and sieving.

Figure 6:
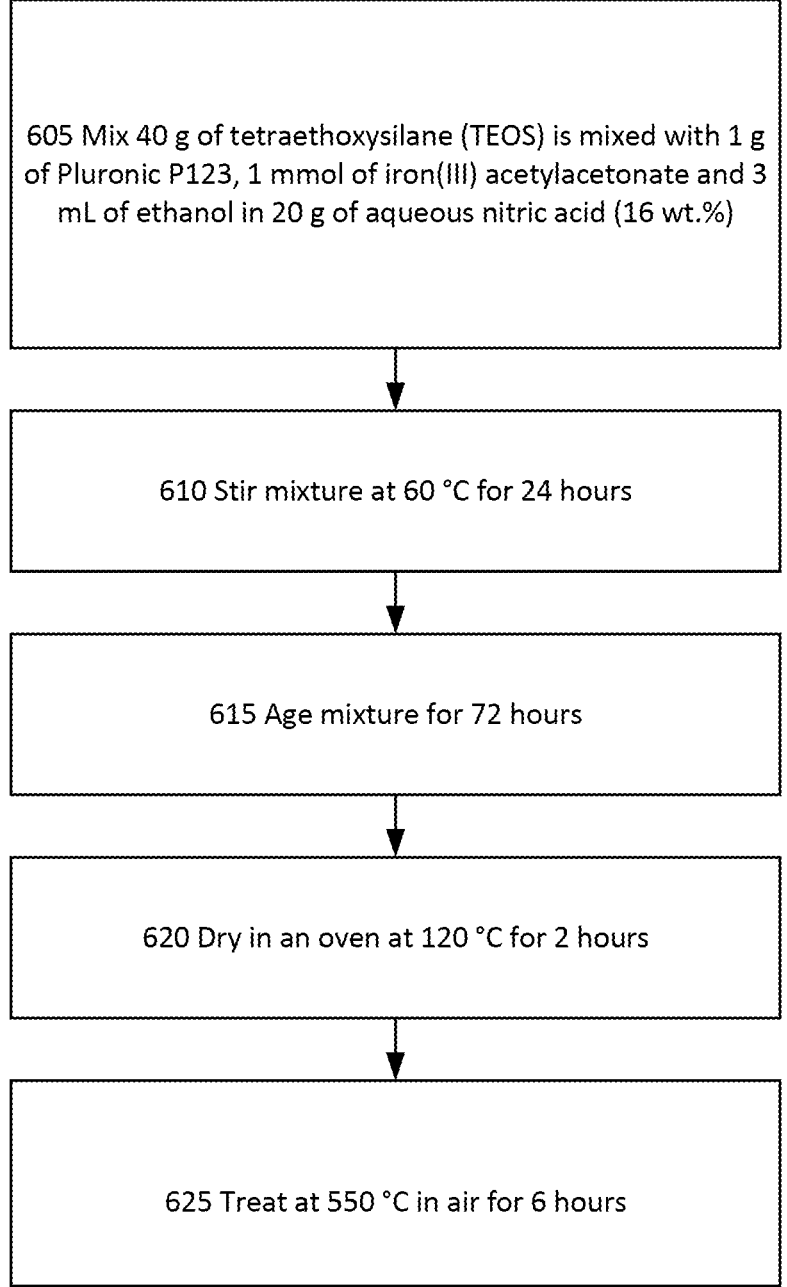
FIG. 6 illustrates a representative process for creating catalyst.

FIG. 6 illustrates a process for creating the catalyst as described with further reference above. The catalyst created by the process in FIG. 6 is referred to as Catalyst F. Catalyst F is prepared using a sol-gel method, which involves mixing 40 grams of tetraethoxysilane (TEOS), 1 gram of Pluronic P123, 1 mmol of iron(III) acetylacetonate, and 3 mL of ethanol in 20 grams of nitric acid (16 wt. %). In action 610, the mixture is stirred at 60° C. for 24 hours. Stirring ensures thorough mixing and interaction among the components. The elevated temperature facilitates the chemical reactions and promotes the formation of a homogenous gel-like material. In action 615, the mixture is aged for 72 hours to undergo further chemical transformations and structural changes. During this time, the gel-like material matures, acquiring the desired properties and structure for effective catalytic performance. In action 620, the resulting gel is dried in an oven at 120° C. for 2 hours to eliminate the excess moisture from the gel and solidify the material. It helps in removing the solvent (in this case, ethanol) and stabilizing the gel structure, transforming it into a solid material. After stirring, aging, and drying, the gel-like material is treated at a temperature of 550° C. in air for 6 hours. This calcination promotes further chemical reactions and structural transformations within the material, removes residual organic components, induces crystallization, and/or enhances the catalytic activity of the material. The resulting material from the stirring, aging, drying, and calcination steps is identified as Catalyst F. Catalyst F is the final product obtained through the sol-gel method and the subsequent thermal treatment. Its composition, structure, and thermal history are tailored to make it suitable for the intended catalytic reaction.

The catalysts described above may be used in, for example, processes for non-oxidative conversion of a hydrocarbon such as natural gas to produce hydrogen and potentially other products. The processes generally comprise contacting the hydrocarbon, e.g., natural gas, with a catalyst described above and/or a mixture of catalysts including at least one of the catalysts described above. The contacting is usually conducted under conditions to convert the hydrocarbon to hydrogen. The process may also produce a light hydrocarbon product such as ethylene, benzene, naphthalene, or any mixture thereof.

The methane dehydrogenation process typically comprises subjecting a methane feed to a catalyst under dehydrogenation conditions. The catalyst comprises amorphous particles of $SiO_2$. The amorphous particles have a particle size with a nominal diameter of from about 5 nm to about 1 cm, preferably from about 50 nm to about 1 mm. The amorphous particles of $SiO_2$ comprise a Lewis acidity sufficient to activate C—H bonds in methane and generate methyl radicals when the catalyst is subjected to methane dehydrogenation conditions.

Typically, hydrogen, ethylene, an aromatic, or any mixture thereof is produced. The aromatics may comprise an aromatic compound such as, for example, benzene, naphthalene, or any mixture thereof. If desired, the hydrogen and/or other products may be separated in any convenient manner.

The dehydrogenation conditions may vary widely depending upon the equipment, the methane feed composition, the specific catalyst composition, and other factors. Useful conditions in some embodiments may comprise a temperature of at least about 800° C. up to about 1200° C. and/or a residence time of from about 0.05 to about 100, or from about 0.05 to about 10 seconds, or from about 1 to about 7 seconds.

The content of methane in the methane feed may vary but in some embodiments it may comprise at least about 70%, or at least about 90% methane. The methane feed may comprise other components in amounts that do not significantly interfere with the process or desired products. In some cases, the methane feed may further comprise nitrogen.

Methane conversion and products produced may also vary depending upon the conditions, equipment, feed, specific catalyst composition, and other factors. In some embodiments, the methane conversion may be at least about 15%. In some embodiments, the process produces a mixture comprising hydrogen, ethylene, and an aromatic or a mixture of aromatics.

In one embodiment, 1.0 g commercial quartz wool with a 9 μm nominal diameter is loosely packed in a 0.35" ID quartz tube. The catalyst bed volume is 12.6 mL. This run is denoted as R046.

In another embodiment, 1.0 g commercial quartz wool with a 9 μm nominal diameter is tightly packed in a 0.35" ID quartz tube. The catalyst bed volume is 3.7 mL. This run is denoted as R047.

In another embodiment, 1.1 g commercial quartz wool with a 9 μm nominal diameter is ball-milled with yttria-stabilized zirconia balls in a roller jar at 25 RPM for 72 hours. The fine powder was compacted and sieved to 20/40 mesh in size before loading into a 0.35" ID quartz tube. The catalyst bed is undiluted, and the volume is 2.2 mL. This run is denoted as R048.

In another embodiment, 1.0 g commercial quartz wool with a 4 μm nominal diameter is tightly packed in a 0.35" ID quartz tube. The catalyst bed volume is 3.9 mL. This run is denoted as R050.

Comparison of the catalyst tests for methane dehydrogenation is summarized in Table 1.

In another embodiment, 3.50 g of commercial quartz wool with a 9 μm nominal diameter is ball-milled with yttria-stabilized zirconia balls in a roller jar at 25 RPM for 72 hours. The fine powder was compacted and sieved to 20/40 mesh in size before loading into a 0.35" ID quartz tube. The catalyst is undiluted, and the volume is 7.0 mL. The run is denoted as R054.

The run is conducted at 1080° C. in a feed gas comprising 90% $CH_4$/10% N2 at a total flow rate of 120 mL/min under ambient pressure. The run length is 911 minutes. The

TABLE 1

Comparison of catalyst tests for methane dehydrogenation (Run condition: 1000° C., 120 mL/min 90% CH4/10% N2 feed gas, ambient pressure)

| Run No. | Catalyst | Treatment | Sizing | Run temperature, ° C. | Catalyst bed vol mL | Residence time, s | $CH_4$ conversion % | Reaction rates μmol gcat$^{-1}$ s$^{-1}$ |
|---|---|---|---|---|---|---|---|---|
| R046 | Corse quartz wool 9 μm nominal | as is | as is | 1000 | 12.6 | 6.30 | 15.6% | 2.2 |
| R047 | Corse quartz wool 9 μm nominal | as is | as is | 1000 | 3.7 | 1.87 | 5.6% | 2.8 |
| R048 | Corse quartz wool 9 μm nominal | dry ball milled | 20/40 mesh | 1000 | 2.2 | 1.08 | 23.7% | 18.9 |
| R050 | Fine quartz wool 4 μm nominal | as is | as is | 1000 | 3.9 | 1.97 | 12.0% | 6.6 |

First, the comparison between R046 and R047 shows that methane conversion for the coarse quartz wool samples increases as the residence time increases, however, the reaction rate for methane conversion is essentially the same for both runs. After the same type of coarse quartz wool is ball-milled to fine powder, the reaction rate is almost 7-fold higher than the case of as-is coarse quartz wool, as shown in total conversion of methane during the run is 21.0%. The overall mass balance is 101.43% and the mass balance for converted CH4 is 101.35%, respectively. The steady state is reached after running for 256 minutes. The product selectivities on a weight basis during the steady state are listed in Table 2. The main products are hydrogen, ethylene and aromatics.

TABLE 2

Weight percentage of each product during the steady state for R054.

| PNA in cold trap | Coke | $H_2$ | $C_2H_4$ | $C_2H_6$ | $C_3H_6$ | $C_4H_{10}$ | $C_4H_8$ | $C_5H_{12}$ | C6+ |
|---|---|---|---|---|---|---|---|---|---|
| 4.65% | 11.50% | 22.22% | 18.77% | 1.69% | 0.55% | 0.13% | 0.26% | 0.42% | 39.81% | the comparison between R048 and R046 and R047. For the fine quartz wool sample as shown in R050, the reaction rate almost triples, as compared to the coarse quartz wool in both R046 and R047. These results demonstrate that quartz wool, as a type of fused silica, is active for methane dehydrogenation. The activity can be enhanced by decreasing its particle size, which likely increases the number of non-hydrogen-bonded silanol groups as described above.

In some aspects, the techniques described herein relate to a catalyst for methane dehydrogenation wherein the catalyst includes: amorphous particles of $SiO_2$; wherein the amorphous particles have a particle size with a nominal diameter of from 5 nm to 1 cm; and wherein the amorphous particles of $SiO_2$ include a Lewis acidity sufficient to activate C—H bonds in methane and generate methyl radicals when the catalyst is subjected to methane dehydrogenation conditions.

In some aspects, the techniques described herein relate to a catalyst, wherein the catalyst does not contain any metals.

In some aspects, the techniques described herein relate to a catalyst wherein the amorphous particles of $SiO_2$ include a plurality of non-hydrogen bonded silanol groups.

In some aspects, the techniques described herein relate to a catalyst wherein an impurity of iron as analyzed by inductively coupled plasma spectroscopy includes less than about 10 ppm.

In some aspects, the techniques described herein relate to a catalyst, wherein the amorphous particles of $SiO_2$ include a plurality of non-hydrogen bonded silanol groups, and wherein an impurity of a Group VIII metal as analyzed by inductively coupled plasma spectroscopy is less than about 10 ppm.

In some aspects, the techniques described herein relate to a catalyst wherein the catalyst is made by a process including reducing the size of a fused silica.

In some aspects, the techniques described herein relate to a catalyst wherein the reducing the size of the fused silica includes increasing a silanol to siloxane ratio.

In some aspects, the techniques described herein relate to a catalyst wherein reducing the size of a fused silica includes grinding, milling, cutting, hot melt extruding, or any combination thereof.

In some aspects, the techniques described herein relate to a catalyst wherein at least a portion of the silanol includes non-hydrogen bonded silanol.

In some aspects, the techniques described herein relate to a catalyst wherein a majority of the silanol includes non-hydrogen bonded silanol.

In some aspects, the techniques described herein relate to a catalyst which further includes sieving the reduced fused silica to a size of from about 5 nm to about 1 cm.

In some aspects, the techniques described herein relate to a methane dehydrogenation process including: subjecting a methane feed to a catalyst under dehydrogenation conditions, wherein the catalyst includes amorphous particles of $SiO_2$, wherein the amorphous particles have a particle size with a nominal diameter of from about 5 nm to about 1 cm, wherein the amorphous particles of $SiO_2$ include a Lewis acidity sufficient to activate C—H bonds in methane and generate methyl radicals when the catalyst is subjected to methane dehydrogenation conditions; and producing hydrogen, alkanes, alkenes, an aromatic, or any mixture thereof.

In some aspects, the techniques described herein relate to a process wherein the aromatic includes benzene, naphthalene, or any mixture thereof.

In some aspects, the techniques described herein relate to a process further including separating hydrogen.

In some aspects, the techniques described herein relate to a process wherein the dehydrogenation conditions include a temperature of at least about 800° C. up to about 1200° C.

In some aspects, the techniques described herein relate to a process wherein the dehydrogenation conditions include a residence time of from about 0.05 to about 100 seconds.

In some aspects, the techniques described herein relate to a process wherein the methane feed includes at least about 70%, or at least about 90% methane.

In some aspects, the techniques described herein relate to a process wherein the methane feed further includes nitrogen.

In some aspects, the techniques described herein relate to a process wherein the methane conversion is at least about 15%.

In some aspects, the techniques described herein relate to a process wherein the process produces a mixture including hydrogen, ethylene, and an aromatic or a mixture of aromatics.

In some aspects, the techniques described herein relate to a process wherein the alkane includes ethane, propane, butanes, pentanes, or any mixture thereof.

In some aspects, the techniques described herein relate to a process wherein the alkene includes ethylene, propylene, butenes, pentenes, unsaturated $C_2$-$C_5$ hydrocarbons, or any mixture thereof.

In some aspects, the techniques described herein relate to a process wherein the aromatic includes other polynuclear aromatic compounds.

Although embodiments of the present invention have been described herein in the context of a particular implementation in a particular environment for a particular purpose, those skilled in the art will recognize that its usefulness is not limited thereto and that the embodiments of the present invention can be beneficially implemented in other related environments for similar purposes. The invention should therefore not be limited by the above described embodiments, method, and examples, but by all embodiments within the scope and spirit of the invention as claimed.

Further, it is to be understood that the terminology used herein is for the purpose of describing particular embodiments only and is not intended to be limiting. The terms "a" or "an" as used herein, are defined as one or more than one. The term "plurality" as used herein, is defined as two or more than two. The term "another" as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

In the invention, various embodiments have been described with references to the accompanying drawings. It may, however, be evident that various modifications and changes may be made thereto, and additional embodiments may be implemented, without departing from the broader scope of the invention as set forth in the claims that follow. The invention and drawings are accordingly to be regarded in an illustrative rather than restrictive sense.

The invention is not to be limited in terms of the particular embodiments described herein, which are intended as illustrations of various aspects. Many modifications and variations can be made without departing from its spirit and scope. Functionally equivalent systems, processes and apparatuses within the scope of the invention, in addition to those enumerated herein, may be apparent from the representative descriptions herein. Such modifications and variations are intended to fall within the scope of the appended claims. The invention is to be limited only by the terms of the appended claims, along with the full scope of equivalents to which such representative claims are entitled.

The preceding description of exemplary embodiments provides non-limiting representative examples referencing numerals to particularly describe features and teachings of different aspects of the invention. The embodiments described should be recognized as capable of implementation separately, or in combination, with other embodiments from the description of the embodiments. A person of ordinary skill in the art reviewing the description of embodiments should be able to learn and understand the different described aspects of the invention. The description of embodiments should facilitate understanding of the invention to such an extent that other implementations, not specifically covered but within the knowledge of a person of skill in the art having read the description of embodiments, would be understood to be consistent with an application of the invention.

EMBODIMENTS

1. A catalyst for methane dehydrogenation wherein the catalyst comprises:
a plurality of amorphous particles of SiO2;
wherein the amorphous particles have a particle size with a nominal diameter of from about 5 nm to about 1 cm; and
wherein the amorphous particles comprise a Lewis acidity sufficient to activate a plurality of C—H bonds in methane and generate methyl radicals when the catalyst is subjected to methane dehydrogenation conditions.
2. The catalyst of embodiment 1, wherein the catalyst does not contain any metals.
3. The catalyst of embodiment 1 wherein the amorphous particles of $SiO_2$ comprise a plurality of non-hydrogen bonded silanol groups.
4. The catalyst of embodiment 1 wherein an impurity of iron as analyzed by inductively coupled plasma spectroscopy comprises less than about 10 ppm.
5. The catalyst of embodiment 1, wherein the amorphous particles of $SiO_2$ comprise a plurality of non-hydrogen bonded silanol groups, and wherein an impurity of a Group VIII metal as analyzed by inductively coupled plasma spectroscopy is less than about 10 ppm.
6. The catalyst of embodiment 1 wherein the catalyst is made by a process comprising reducing the size of a plurality of fused silica.
7. The catalyst of embodiment 6 wherein the reducing the size of the fused silica comprises increasing a silanol to siloxane ratio.
8. The catalyst of embodiment 6 wherein reducing the size of a fused silica comprises at least grinding, milling, cutting, hot melt extruding, or any combination thereof.
9. The catalyst of embodiment 7 wherein at least a portion of the silanol comprises non-hydrogen bonded silanol.
10. The catalyst of embodiment 9 wherein a majority of the silanol comprises non-hydrogen bonded silanol.
11. The catalyst of embodiment 6 which further comprises sieving the reduced fused silica to a size of from about 5 nm to about 1 cm.
12. A methane dehydrogenation process comprising:
subjecting a methane feed to a catalyst under dehydrogenation conditions, wherein the catalyst comprises a plurality of amorphous particles of $SiO_2$,
wherein the amorphous particles have a particle size with a nominal diameter of from about 5 nm to about 1 cm,
wherein the amorphous particles comprise a Lewis acidity sufficient to activate C—H bonds in methane and generate methyl radicals when the catalyst is subjected to methane dehydrogenation conditions; and
producing hydrogen, one or more alkanes, one or more alkenes, one or more alkynes, one or more aromatics, or any mixture thereof.
13. The process of embodiment 12 wherein the aromatic comprises benzene, naphthalene, or any mixture thereof.

14

14. The process of embodiment 12 further comprising separating hydrogen from the catalyst.
15. The process of embodiment 12 wherein the dehydrogenation conditions comprise a temperature of at least about 800° C. up to about 1200° C.
16. The process of embodiment 12 wherein the dehydrogenation conditions comprise a residence time of from about 0.05 to about 100 seconds.
17. The process of embodiment 12 wherein the methane feed comprises at least about 70% methane.
18. The process of embodiment 17 wherein the methane feed further comprises nitrogen.
19. The process of embodiment 12 wherein the methane conversion is at least 15%.
20. The process of embodiment 12 wherein the process produces a mixture comprising hydrogen, ethylene, acetylene, and an aromatic or a mixture of aromatics.
21. The process of embodiment 12 wherein the alkane comprises ethane, propane, butanes, pentanes, or any mixture thereof.
22. The process of embodiment 12 wherein the alkene comprises ethylene, propylene, butenes, pentenes, unsaturated $C_2$-$C_5$ hydrocarbons, or any mixture thereof.
23. The process of embodiment 12 wherein the alkyne comprises acetylene, propyne, or any mixture thereof.
24. The process of embodiment 13 wherein the aromatic further comprises other polynuclear aromatic compounds.

What is claimed is:
1. A catalyst for methane dehydrogenation wherein the catalyst comprises:
a plurality of amorphous particles of SiO2 wherein the amorphous particles of $SiO_2$ comprise a non-metallic derivative of fused silica;
wherein the amorphous particles have a particle size with a nominal diameter of from about 5 nm to about 1 cm; and
wherein the amorphous particles comprise a Lewis acidity sufficient to activate a plurality of C—H bonds in methane and generate methyl radicals when the catalyst is subjected to methane dehydrogenation conditions.
2. The catalyst of claim 1, wherein the catalyst does not contain any metals.
3. The catalyst of claim 1 wherein the amorphous particles of $SiO_2$ comprise a plurality of non-hydrogen bonded silanol groups.
4. The catalyst of claim 1 wherein an impurity of iron as analyzed by inductively coupled plasma spectroscopy comprises less than about 10 ppm.
5. The catalyst of claim 1, wherein the amorphous particles of $SiO_2$ comprise a plurality of non-hydrogen bonded silanol groups, and wherein an impurity of a Group VIII metal as analyzed by inductively coupled plasma spectroscopy is less than about 10 ppm.
6. The catalyst of claim 1 wherein the catalyst is made by a process comprising reducing the size of a plurality of fused silica.
7. The catalyst of claim 6 wherein the reducing the size of the fused silica comprises increasing a silanol to siloxane ratio.
8. The catalyst of claim 6 wherein reducing the size of a fused silica comprises at least grinding, milling, cutting, hot melt extruding, or any combination thereof.
9. The catalyst of claim 7 wherein at least a portion of the silanol comprises non-hydrogen bonded silanol.
10. The catalyst of claim 9 wherein a majority of the silanol comprises non-hydrogen bonded silanol.

11. The catalyst of claim 6 which further comprises sieving the reduced fused silica to a size of from about 5 nm to about 1 cm.

12. A methane dehydrogenation process comprising:

subjecting a methane feed to a catalyst under dehydrogenation conditions, wherein the catalyst comprises a plurality of amorphous particles of $SiO_2$, wherein the amorphous particles of $SiO_2$ comprise a non-metallic derivative of fused silica and wherein the catalyst does not contain any metals, wherein the amorphous particles have a particle size with a nominal diameter of from about 5 nm to about 1 cm, wherein the amorphous particles comprise a Lewis acidity sufficient to activate C—H bonds in methane and generate methyl radicals when the catalyst is subjected to methane dehydrogenation conditions; and producing hydrogen, one or more alkanes, one or more alkenes, one or more alkynes, one or more aromatics, or any mixture thereof.

13. The process of claim 12 wherein the aromatic comprises benzene, naphthalene, or any mixture thereof.

14. The process of claim 12 further comprising separating hydrogen from the catalyst.

15. The process of claim 12 wherein the dehydrogenation conditions comprise a temperature of at least about 800° C. up to about 1200° C.

16. The process of claim 12 wherein the dehydrogenation conditions comprise a residence time of from about 0.05 to about 100 seconds.

17. The process of claim 12 wherein the methane feed comprises at least about 70% methane.

18. The process of claim 17 wherein the methane feed further comprises nitrogen.

19. The process of claim 12 wherein the methane conversion is at least 15%.

20. The process of claim 12 wherein the process produces a mixture comprising hydrogen, ethylene, acetylene, and an aromatic or a mixture of aromatics.

21. The process of claim 12 wherein the alkane comprises ethane, propane, butanes, pentanes, or any mixture thereof.

22. The process of claim 12 wherein the alkene comprises ethylene, propylene, butenes, pentenes, unsaturated $C_2$-$C_5$ hydrocarbons, or any mixture thereof.

23. The process of claim 12 wherein the alkyne comprises acetylene, propyne, or any mixture thereof.

\* \* \* \* \*